United States Patent [19]

Tomaschke et al.

[11] Patent Number: 5,254,261
[45] Date of Patent: Oct. 19, 1993

[54] INTERFACIALLY SYNTHESIZED REVERSE OSMOSIS MEMBRANES AND PROCESSES FOR PREPARING THE SAME

[75] Inventors: John E. Tomaschke, San Diego; Istvan E. Ary, Vista, both of Calif.

[73] Assignee: Hydranautics, San Diego, Calif.

[21] Appl. No.: 838,515

[22] Filed: Feb. 19, 1992

Related U.S. Application Data

[63] Continuation-in-part of Ser. No. 744,194, Aug. 12, 1991, abandoned.

[51] Int. Cl.$^5$ .............................................. B01D 67/00
[52] U.S. Cl. ................................. 210/654; 210/490; 210/500.38
[58] Field of Search .................... 210/560.38, 654, 490, 210/500.34, 500.39; 427/245; 514/492, 169, 172; 528/170; 264/41, 47

[56] References Cited

U.S. PATENT DOCUMENTS

| | | | |
|---|---|---|---|
| 3,904,519 | 9/1975 | McKinney, Jr. et al. | 210/23 |
| 3,996,318 | 12/1976 | van Heuven | 264/5 |
| 4,277,344 | 7/1981 | Cadotte | 210/654 |
| 4,520,044 | 5/1985 | Sundet | 427/244 |
| 4,529,646 | 7/1985 | Sundet | 428/315.5 |
| 4,544,484 | 10/1985 | Sundet | 264/41 X |
| 4,619,767 | 10/1986 | Kamiyama et al. | 210/490 |
| 4,626,468 | 12/1986 | Sundet | 428/315.5 |
| 4,643,829 | 2/1987 | Sundet | 210/500.33 |
| 4,661,254 | 4/1987 | Zupancic | 210/490 |
| 4,749,488 | 6/1988 | Arthur et al. | 210/490 |
| 4,761,234 | 8/1988 | Uemura et al. | 210/500.38 |
| 4,783,346 | 11/1988 | Sundet | 427/244 |
| 4,828,708 | 5/1989 | Bray | 210/654 |
| 4,872,984 | 10/1989 | Tomaschke | 210/500.38 |
| 4,948,507 | 8/1990 | Tomaschke | 210/500.38 |
| 5,147,553 | 9/1992 | Waite | 210/500.34 X |

FOREIGN PATENT DOCUMENTS 62-247808  10/1987  Japan .

OTHER PUBLICATIONS

J. E. Cadotte, "Evolution of Composite Reverse Osmosis Membranes," *Material Science of Synthetic Membranes*, Chapter 12, pp. 273–294, American Chemical Society Symposium Series (185).

S. D. Arthur, "Structure-Property Relationship in a Thin Film Composite Reverse Osmosis Membrane," *Journal of Membrane Science*, 46:243–260, Elsevier (1989).

*Primary Examiner*—Frank Spear
*Attorney, Agent, or Firm*—Panitch Schwarze Jacobs & Nadel

[57] ABSTRACT

Water permeable reverse osmosis membranes are prepared by interfacially polymerizing on a microporous support an essentially monomeric polyamine reactant having at least two amine functional groups per reactant molecule, and an essentially monomeric amine-reactive polyfunctional single ring cycloaliphatic acyl halide having fewer than six carbon atoms per ring and having on the average at least about 2.2 acyl halide groups per reactant molecule. The polymerization is preferably carried out in the presence of a monomeric amine salt, which increases the flux rate of the resulting membrane. In addition, an aromatic polyfunctional acyl halide may be used in conjunction with the cycloaliphatic acyl halide in order to increase salt rejection rates. Preferred cycloaliphatic acyl halides are 1-cis, 2-trans, 3-cis, 4-trans-cyclopentane tetracarboxylic acid chloride, 1-cis, 2-trans, 3-cis, 4-trans-cyclobutane tetracarboxylic acid chloride and 1-cis, 2-trans, 4-cis-cyclopentane tricarboxylic acid chloride. The preparation of novel alternating cis/trans isomers of cycloaliphatic polycarboxylic acid halides is carried out using metal salts of the all-cis polycarboxylic acids.

55 Claims, No Drawings

INTERFACIALLY SYNTHESIZED REVERSE OSMOSIS MEMBRANES AND PROCESSES FOR PREPARING THE SAME

CROSS-REFERENCE TO RELATED APPLICATION

This application is a continuation-in-part of copending application Ser. No. 07/744,194, filed Aug. 12, 1991, under the same title, now abandoned.

FIELD OF THE INVENTION

The present invention relates to interfacially synthesized reverse osmosis membranes useful for the separation of fluid mixtures and solutions. In particular, the present invention is directed to polyamide water permeable membranes which are useful for desalination of an aqueous solution. The present invention also relates to processes for preparing the membranes.

BACKGROUND OF THE INVENTION

It is known that dissolved substances can be separated from their solvents by the use of selective membranes. For example, of great practical interest is the removal of salt from water by reverse osmosis. The efficiency and economy of such removal is of tremendous economic significance in order to provide potable water from brackish or sea water for household or agricultural use. A critical factor in desalination is the performance of the membrane in terms of salt rejection, i.e., the reduction in salt concentration across the membrane, and flux, i.e., the flow rate across the membrane. For practical applications, the flux should be on the order of greater than about 10 gallons/ft$^2$-day (gfd) at a pressure of about 55 atmospheres for sea water and about 15 gfd at a pressure of about 15 atmospheres for brackish water. More preferably, commercial applications now require fluxes greater than about 25 gfd (about 1.0 m$^3$/m$^2$-day) at a pressure of about 15 atmospheres for brackish water. Moreover, salt rejections greater than 99% are required. The continuing goal of research and development in this area is to develop membranes having increased flux and/or salt rejection which are useful in desalination.

Among the known membranes used in desalination are included a large number of various types of polyamides which are prepared by a variety of methods. Of particular interest within this broad group of polyamide membranes are crosslinked aromatic polyamide membranes. The crosslinked aromatic polyamide membranes include, for example, those disclosed in the following U.S. Patents.

U.S. Pat. No. 3,904,519, issued to McKinney et al., discloses reverse osmosis membranes of improved flux prepared by crosslinking aromatic polyamide membranes using crosslinking agents and/or irradiation. The polyamides are prepared, for example, by the interfacial polymerization of amine groups and carboxyl groups followed by crosslinking.

U.S. Pat. No. 3,996,318, issued to van Heuven, teaches the production of aromatic polyamide membranes, wherein crosslinking is achieved using a reactant having a functionality of three or greater.

U.S. Pat. No. 4,277,344, issued to Cadotte, describes a reverse osmosis membrane which is the interfacial reaction product of an aromatic polyamine having at least two primary amine substituents with an aromatic acyl halide having at least three acyl halide substituents. The preferred membrane is made of a poly(phenylenediamine trimesamide) film on a porous polysulfone support.

U.S. Pat. No. 4,828,708, issued to Bray, discloses a similar membrane in which a major portion of the trifunctional aromatic acyl halide is replaced by the difunctional aromatic acyl halide-isophthaloyl chloride.

U.S. Pat. No. 4,529,646, issued to Sundet, shows a membrane similar to U.S. Pat. No. 4,277,344 in which all or a portion of the trifunctional aromatic acyl halide is replaced by cyclohexane-1,3,5-tricarbonyl chloride. Similar membranes are disclosed in U.S. Pat. Nos. 4,520,044; 4,544,484; 4,626,468; 4,643,829; and 4,783,346, each issued to Sundet (du Pont).

U.S. Pat. No. 4,761,234, issued to Uemura et al., shows a membrane similar to U.S. Patent 4,277,344 in which aromatic tri- or higher aromatic amines are employed U.S. Pat. No. 4,661,254, issued to Zupanic et al., discloses a reverse osmosis composite membrane formed by the interfacial polymerization of a triaryl triamine with an aromatic carboxylic acid chloride.

U.S. Pat. No. 4,619,767, issued to Kamiyama et al., describes membranes prepared by crosslinking polyvinyl alcohol and secondary di- or higher amines with polyfunctional crosslinking agents. Both aromatic and aliphatic amine components are disclosed.

U.S. Pat. No. 4,749,488, issued to Arthur et al., discloses membranes of polyphenylene tetrahydrofuran-2,3,4,5-tetracarboxamide which may also include isophthalamide or terephthalamide units. Interestingly, Examples 19 and 20 of this patent describe preparation of a membrane prepared by reacting all-cis cyclopentane-1,2,3,4-tetracarbonyl tetrachloride (CPTC) with meta-phenylene diamine (MPD) which showed totally unacceptable salt rejection results (Examples 21 and 22) compared to the membranes claimed in the patent.

U.S. Pat. Nos. 4,872,984 and 4,948,507, issued to Tomaschke and assigned to the same assignee as the present application, describe the interfacial synthesis of reverse osmosis membranes from an essentially monomeric polyamine having at least two amine functional groups and an essentially monomeric polyfunctional acyl halide having at least about 2.2 acyl halide groups per reactant molecule, in the presence of a monomeric amine salt. Both aromatic and aliphatic polyamines and polyfunctional acyl halides are disclosed.

Interesting reviews and comparisons of various composite reverse osmosis membranes are included in J. E. Cadotte, "Evolution of Composite Reverse Osmosis Membranes," *Materials Science of Synthetic Membranes* Chapter 12, pp. 273-294, American Chemical Society Symposium Series (1985) and S. D. Arthur, "Structure-Property Relationship in a Thin Film Composite Reverse Osmosis Membrane," *Journal of Membrane Science*, 46:243-260, Elsevier (1989).

While some of the above-referenced membranes are commercially useable, the goal of the industry continues to be to develop membranes that have better flux and salt rejection characteristics in order to reduce costs and increase efficiency of operation.

SUMMARY OF THE INVENTION

Accordingly, an object of the present invention is to provide an interfacially synthesized reverse osmosis membrane which has high salt rejection and excellent flux.

This and other objects of the present invention, which will be apparent from the detailed description of the present invention provided hereinafter, have been met by a water permeable membrane prepared by interfacially polymerizing, on a microporous support, (1) an essentially monomeric polyamine reactant having at least two amine functional groups, and (2) an essentially monomeric amine-reactive reactant comprising a polyfunctional single ring cycloaliphatic acyl halide having fewer than 6 carbon atoms in the ring, or mixtures of these acyl halides, wherein the amine-reactive reactant has, on the average, at least about 2.2 acyl halide groups per reactant molecule. A particularly preferred amine-reactive reactant is the cis-trans-cis-trans (ctct) isomer of 1,2,3,4-cyclopentane tetracarboxylic acid chloride.

In a preferred embodiment of the present invention, the above interfacial polymerization is carried out in the presence of a monomeric amine salt by either (a) a solution containing both a monomeric amine salt and a polyamine being coated on a microporous support prior to coating with a solution of a polyfunctional acyl halide, or (b) a monomeric amine salt solution being coated on a microporous support prior to coating with a polyamine solution and a polyfunctional acyl halide solution.

In another preferred embodiment, up to about 90 weight percent of the cycloaliphatic acyl halide reactant is replaced by at least one essentially monomeric, aromatic polyfunctional acyl halide having a functionality of at least two, preferably isophthaloyl chloride, trimesoyl chloride, and/or terephthaloyl chloride.

The resulting polymerizations yield ultrathin membranes on the microporous support. These membranes have excellent salt rejection and flux and are suitable for desalination applications.

Novel alternating cis/trans isomers (e.g., ctct or ctc) of the polyfunctional cycloaliphatic acyl halides, and methods of preparing these isomers via metal salts are also part of the present invention.

DETAILED DESCRIPTION OF PREFERRED EMBODIMENTS

The membranes of the present invention may be formed by various methods of interfacial polymerization, a number of which are known in the art. Presently preferred are the methods described in prior U.S. Pat. Nos. 4,872,984 and 4,948,507, the disclosures of which are incorporated herein by reference. While the present invention will now be described herein with reference to the preferred method in which the polymerization is carried out in the presence of a monomeric amine salt, it will be understood that the following methods could be carried out without the presence of the monomeric amine salt, which is used in the methods of the prior above-mentioned patents.

In one embodiment, the objects of the present invention have been met by a water permeable membrane produced by the process comprising the steps of:

(a) coating a microporous support with an aqueous solution comprising (i) an essentially monomeric polyamine reactant having at least two amine functional groups and (ii) a monomeric amine salt, to form a liquid layer on said microporous support;

(b) contacting said liquid layer with an organic solvent solution of an essentially monomeric amine-reactive reactant comprising a polyfunctional single ring cycloaliphatic acyl halide having fewer than six carbon atoms in the ring, or mixture thereof, wherein the amine-reactive reactant has, on the average, at least about 2.2 acyl halide groups per reactant molecule; and (c) drying the product of step (b) so as to form said water permeable membrane.

In a second embodiment, the water permeable membrane is produced by the process comprising the steps of:

(a) coating a microporous support with a first aqueous solution comprising a monomeric amine salt to form a monomeric amine salt layer on said microporous support;

(b) coating said monomeric amine salt layer with a second aqueous solution comprising an essentially monomeric polyamine reactant having at least two amine functional groups to form a liquid layer on said monomeric amine salt layer;

(c) coating said liquid layer with an organic solvent solution of an essentially monomeric amine-reactive reactant, comprising a polyfunctional single ring cycloaliphatic acyl halide having fewer than six carbon atoms in the ring, or mixture thereof, wherein the amine-reactive reactant has, on the average, at least about 2.2 acyl halide group per reactant molecule; and (d) drying the product of step (c) so as to form said water permeable membrane.

The particular microporous support employed in the present invention is not critical thereto. Examples of such microporous supports useful in the present invention include those made of a polyarylether sulfone, such as a polysulfone and a polyether sulfone; a polyimide; or a polyvinylidene fluoride. The microporous support is preferably made of a polyarylether sulfone. The thickness of the microporous support is not critical to the present invention. Generally, the thickness of the microporous support is about 25 to 125 $\mu$m, preferably about 40 to 75 $\mu$m.

The essentially monomeric polyamine reactant employed in the present invention has at least two amine functional groups, preferably 2 to 3 amine functional groups, per molecule. The amine functional group is a primary or secondary amine functional group, preferably a primary amine functional group. The polyamine reactant may be aromatic or cycloaliphatic.

The particular polyamine reactant employed in the present invention is not critical thereto. Examples of such polyamine reactants include aromatic primary diamines, such as m-phenylenediamine and p-phenylenediamine and substituted derivatives thereof, wherein the substitutent includes, e.g., an alkyl group, such as a methyl group or an ethyl group; an alkoxy group, such as a methoxy group or an ethoxy group; a hydroxy alkyl group; a hydroxy group or a halogen atom; aromatic primary triamines, such as 1,2,4-triaminobenzene; aromatic secondary diamines, such as N,N'-diphenylethylene diamine; cycloaliphatic primary diamines, such as cyclohexane diamine; cycloaliphatic secondary diamines, such as piperazine and trimethylene dipiperidine; and xylylene diamines, such as m-xylylene diamine. The preferred aromatic polyamine reactants employed in the present invention are aromatic primary diamines, more preferably m-phenylenediamine (MPD).

The amine-reactive reactant used in the present invention is an essentially monomeric, polyfunctional single ring cycloaliphatic acyl halide having fewer than 6 carbon atoms on the ring, or a mixture of such acyl halides, wherein the amine-reactive reactant has, on the average, at least about 2.2, and preferably, on the average, about three to about four acyl halide groups per reactant molecule. Preferred cycloaliphatic acyl halides for use in the present invention include the tetra-substituted acyl chlorides of cyclopentane tetracarboxylic acid and cyclobutane tetracarboxylic acid, namely 1,2,3,4-cyclopentane tetracarboxylic acid chloride (CPTC) and 1,2,3,4-cyclobutane tetracarboxylic acid chloride (CBTC) and the tri-substituted acyl chlorides of cyclopentane tricarboxylic acid and cyclobutane tricarboxylic acid, namely, 1,2,4-cyclopentane tricarboxylic acid chloride (CPTrC) and 1,2,3-cyclobutane tricarboxylic acid chloride (CBTrC).

These cycloaliphatic acyl halides are normally formed as the all-cis stereoisomer or as mixtures containing partial trans stereoisomer. However, the preferred isomeric species of the cycloaliphatic acid halides for use in the present invention are the 1-cis, 2-trans, 3-cis, 4-trans (ctct) isomers of CPTC and CBTC, the 1-cis, 2-trans, 4-cis (ctc) isomer of CPTrC and the 1-cis, 2-trans, 3-cis (ctc) isomer of CBTrC. However, it will be understood that other halides or other equivalent substituent groups or other numbers of substituents or other stereoisomers, such as the all-cis or 1-cis, 2-trans, 3-cis, 4-cis (ctcc) isomers of CPTC and CBTC, may be used according to the invention.

Methods of making the polyfunctional single ring cycloaliphatic acid halide and synthetic intermediates are known in the art, for example from *New Experimental Chemistry Lectures*, Vol. 14, pages 1106-1108, edited by the Japan Chemistry Association and in German Patent No. 2 105 010 of Aubry et al. which discloses preparation of the ctcc isomer of 1,2,3,4-cyclopentane tetracarboxylic acid from the all-cis form by refluxing for 72 hours in boiling water.

A method of preparation of an all-cis cycloaliphatic tetracarboxylic acid chloride, as described more fully below in Preparation Example A, comprises reacting a cycloaliphatic polycarboxylic acid with phosphorous pentahalide or other suitable halogenation reagents in an organic solvent with heat, stirring and reflux, followed by filtering and solvent extraction.

A method of preparation of a 1-cis, 2-trans, 3-cis, 4-trans cycloaliphatic tetracarboxylic acid halide, as described more fully below in Preparation Example B, comprises forming an aqueous solution of a metal salt (e.g., alkali, alkaline earth or transition metal salt) of an all-cis cycloaliphatic tetracarboxylic acid and heating at high temperature (at least 150° C. and preferably at least 200° C.) and pressure (e.g., autoclaving), followed by filtering, extraction with organic solvents and drying to form the ctct isomer of the cycloaliphatic tetracarboxylic acid. The product is then reacted with a halogenation reagent in an organic solvent with heat, stirring and reflux, followed by filtering and solvent extraction.

A method of preparation of a cycloaliphatic tricarboxylic acid halide, as described more fully below in Preparation Example C, comprises oxidation of 5-vinyl 2-norbornene by reacting the compound with sodium periodate in the presence of a catalyst in a polar solvent with heat, stirring and reflux followed by drying, solvent extractions, filtering and more drying. The product is then reacted with a halogenation reagent in an organic solvent with heat, stirring and reflux, followed by filtering and solvent extraction.

A method of preparation of a 1-cis, 2-trans, 4-cis cycloaliphatic tricarboxylic acid halide, as described more fully below in Preparation Example D, comprises forming an aqueous solution of a metal salt (e.g., alkali, alkaline earth or transition metal salt) of an all-cis cycloaliphatic tricarboxylic acid and heating at high temperature (at least 150° C. and preferably at least 200° C.) and pressure (e.g., autoclaving), followed by filtering, extraction with organic solvents and drying to form the ctc isomer of the cycloaliphatic tricarboxylic acid. The product is then reacted with a halogenation reagent phosphorous pentahalide in an organic solvent with heat, stirring and reflux, followed by filtering and solvent extraction.

In addition to the cycloaliphatic acyl halide reactant described above, the amine-reactive reactant may also include in admixture with the cycloaliphatic acyl halide an essentially monomeric polyfunctional aromatic acyl halide having at least about two acyl halide groups per reactive molecule. That is, up to about 90 weight percent, and preferably about 0 to 70 weight percent, of the cycloaliphatic acyl halide may be substituted with one or more aromatic acyl halides.

Examples of such aromatic acyl halides include isophthaloyl halide, trimesoyl halide, terephthaloyl halide, and mixtures thereof. The preferred aromatic acid halides employed in the present invention with the cycloaliphatic acyl halide are isophthaloyl chloride (IPC), trimesoyl chloride (TMC) and/or terephthaloyl chloride (TPC).

The monomeric amine salt employed in the present invention may be a salt of a monomeric amine and an acid, and is preferably a salt of a tertiary amine and a strong acid. As used herein, a strong acid is an acid which reacts essentially completely with water to give a hydronium ion. Examples of such strong acids include an aromatic sulfonic acid; an aliphatic sulfonic acid; a cycloaliphatic sulfonic acid, such as camphorsulfonic acid; trifluoroacetic acid; nitric acid; hydrochloric acid; and sulfuric acid.

The particular monomeric amine salt employed in the present invention is not critical thereto and may be any aliphatic, alkoxy, cycloaliphatic, heterocyclic or alkanol monomeric amine salt. Preferred monomeric amine salts employed in the invention are represented by formulas (I) and (II) below:

 (I)

 (II)

wherein $R_1$, $R_2$, $R_3$ and $R_4$, which may be the same or different, each represents a hydrocarbon: X represents a member selected from the group consisting of a halide, a nitrate, a sulfate, a phosphate, a sulfonate, a carboxylate, a halogenated carboxylate and an oxygenated haloacid derivative; and HX represents a strong acid which forms a water soluble salt with

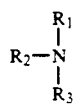

In formula (I), the hydrocarbons represented by $R_1$, $R_2$ and $R_3$ preferably have a total number of carbon atoms of 3 to 9, more preferably, 3 to 6. In formula (II), the hydrocarbons represented by $R_1$, $R_2$, $R_3$ and $R_4$, preferably have a total number of carbon atoms Of 4 to 16, more preferably, 4 to 13. The hydrocarbon may be, e.g., a straight or branched chain, substituted or unsubstituted alkyl group, alkoxy group, alkanol group or benzyl group. Further, in formula (I), two or more of $R_1$, $R_2$ and $R_3$ may combine together to form a ring.

More preferably, the monomeric amine salt employed in the present invention is a water soluble salt of a strong acid and a tertiary amine selected from the group consisting of a trialkylamine, such as trimethylamine, triethylamine, tripropylamine; an N-alkylcycloaliphatic amine, such as 1-methylpiperidine; an N,N-dialkylamine, such as N,N-dimethylethylamine and N,N-diethylmethylamine; an N,N-dialkyl ethanolamine, such as N,N-dimethylethanolamine; a bicyclic tertiary amine, such as 3-quinuclidinol and mixtures thereof, or a quaternary amine selected from at least one member of the group consisting of a tetraalkylammonium hydroxide, such as, tetramethylammonium hydroxide, tetraethylammonium hydroxide, and tetrapropylammonium hydroxide; a benzyltrialkylammonium hydroxide, such as benzyltrimethylammonium hydroxide, benzyltriethylammonium hydroxide, and benzyltripropylammonium hydroxide; and mixtures thereof. A particularly preferred monomeric amine salt is the amine salt of triethylamine amine and camphorsulfonic acid (TEACSA).

The monomeric amine salt is employed either as a solid, which is water soluble, or as an aqueous solution having dissolved therein the monomeric amine salt. The monomeric amine salt is preferably employed as an aqueous solution thereof. The monomeric amine used to prepare the monomeric amine salt preferably has a pKa of more than about 8, more preferably about 8 to 13, most preferably about 9 to 13.

In one embodiment of the present invention, the microporous support is coated with a first aqueous solution containing generally about 0.25 to 10.0 wt. % of a monomeric amine salt, preferably about 1.0 to 8.0 wt. % of a monomeric amine salt. The first aqueous solution is preferably adjusted to a pH of about 5.5 to 13, more preferably about 6 to 12, by controlling the concentration of the acid or the monomeric amine. In this case, the second aqueous solution containing the polyamine reactant generally has a pH of about 5 to 12, preferably about 6 to 12. Further, in this case, where the monomeric amine salt and the polyamine reactant are separately coated on the microporous support, the coating amount is generally adjusted so that the molar ratio of the monomeric amine salt to the polyamine reactant is about 0.1 to 4.0, preferably about 0.3 to 1.4.

In order to save a step in the process of the present invention, the above aqueous solution of the monomeric amine salt can also contain the polyamine reactant. In this case the aqueous solution is generally adjusted to a pH of about 5.5 to 13, preferably about 6 to 12. Further, in this case, the molar ratio of the monomeric amine salt to the polyamine reactant is also generally adjusted to about 0.1 to 4.0, preferably about 0.3 to 1.4

The choice of pH depends on the base strength of the particular reactive polyamine employed. In general, the above-described lower range pH value of the reactive polyamine solution should be about the same as the pKa of the particular polyamine employed and the higher range pH value should be about the same as the particular unadjusted free base aqueous pH. In the case of aromatic polyamines, the pKa is in the range of about 4 to 7, whereas with cycloaliphatic polyamines, the pKa is in the range of about 8 to 11.

The above aqueous solutions are coated by any well known means, such as dipping, spraying, roller coating, rod coating or cloth sheet coating and allowed to remain in place generally for about 5 seconds to 10 minutes, preferably about 20 seconds to 4 minutes.

If desired, the aqueous solutions may contain a surfactant for more improved results. The particular surfactant employed in the present invention is not critical thereto. Examples of such surfactants include sodium dodecyl benzene sulfonate (SDBS), sodium dodecyl sulfate (SDS), sodium lauryl sulfate (SLS) or mixtures thereof. The surfactants are generally employed at a concentration of about 0.01 to 0.5 wt. %, preferably about 0.1 to 0.25 wt. %.

After forming a liquid layer containing the monomeric amine salt and the polyamine reactant, a second layer of an organic solvent solution containing the essentially monomeric amine-reactive reactant is coated thereon. Generally, the organic solvent solution contains about 0.05 to 5.0 wt./vol. %, preferably about 0.07 to 0.7 wt./vol. % of the amine-reactive reactant. It is preferable to employ an about 5 to 200, preferably an about 20 to 150, molar excess of the polyamine reactant to the amine-reactive reactant.

The organic solvent employed in the present invention is one which is non-miscible with water. The particular organic solvent employed in the present invention is not critical thereto. Examples of such organic solvents include alkanes, such as hexane and nonane; cycloalkanes, such as cyclohexane; and halogenated derivatives thereof, such as FREON ® (E.I. duPont de Nemours), including 1,1,2-trichlorotrifluoroethane; and mixtures thereof. The preferred organic solvents employed in the present invention are alkanes having from 6 to 12 carbon atoms.

The organic solvent containing the amine-reactive reactant is coated by any well known means, such as dipping or spraying, and allowed to remain in place generally for about 3 seconds to 20 minutes, preferably about 5 seconds to 30 seconds.

After each step of coating the aqueous and organic solvent solutions, the excess solutions are removed. Then, after the last coating and draining step, the resulting product is dried to form a water permeable membrane. The resulting product is generally dried in an oven at about room temperature to 140° C., preferably about 70° to 125° C. for about 1 to 10 minutes, preferably about 2 to 8 minutes. In this manner, a polyamide layer is formed on the microporous support. The thickness of the resulting polyamide layer is generally about 0.05 to 1.0 um, preferably about 0.15 to 0.5 um.

The following examples are provided for illustrative purposes only and are in no way intended to limit the scope of the present invention. Unless otherwise indicated below, all percentages (%) of ingredients are percent by weight (i.e., wt./wt. %).

PREPARATION EXAMPLE A 1,2,3,4-cyclopentane tetracarboxylic acid chloride (CPTC) was prepared by adding 75 grams (0.305 mole) of all cis-1,2,3,4-cyclopentane tetracarboxylic acid to approximately 800 ml n-heptane containing 510 grams (2.44 moles) of phosphorous pentachloride in a 2 liter round bottom flask fitted with thermometer, heating mantle, reflux condenser, and magnetic stirrer. The temperature of reaction was increased gradually from 20° C. to 95° C. reflux over a three hour period. Reflux was maintained at 95° C. for an additional 2½ hours at which point no HCl gas evolution was detected.

The obtained yellow solution was suction filtered through a coarse paper and then roto-evaporated to an oil several times using additional portions of heptane solvent. The amber colored oil was given high vacuum for an additional ½ hour and then extracted with several 200 ml portions of anhydrous heptane to yield a 1% stock solution which may be diluted with further solvent to provide the desired concentration of reaction solution. Final yield of CPTC was 17.9 grams.

The synthesis of 1,2,3,4-cyclobutane tetracarboxylic acid chloride (CBTC) was carried out in substantially the same manner.

PREPARATION EXAMPLE B 1-cis, 2-trans, 3-cis, 4-trans-cyclopentane tetracarboxylic acid chloride (ctct CPTC) was prepared by the following method.

Isomerization of all-cis CPTA to ctct CPTA Intermediate 10 g (40.6 mmoles) of all-cis-1,2,3,4-cyclopentane tetracarboxylic acid (CPTA) dissolved in 100 ml deionized water was added to a solution containing 166 mmoles of lithium hydroxide monohydrate. The solution was loaded into a 316 stainless steel Parr reactor equipped with stirring blade, pressure gauge, thermocouple and an external heating mantle. The solution was heated at 250° C. for 6 hours during which a pressure of approximately 540 psi was maintained. The solution was filtered to remove insoluble material and the aqueous solution evaporated at 60° C. under a vacuum of 30 mm Hg. The last traces of water were removed by treating the pasty solids with isopropanol followed by a portion of toluene. A non-hygroscopic white powder was obtained after drying for 4 hours under a vacuum of approximately 0.1 mm Hg.

Determination of ctct CPTA Yield

The yield of the tetralithium ctct CPTA isomer was determined by gas chromotography analysis of the tetramethyl ester derivatives of the reaction products. An aqueous solution of the salt of the cycloaliphatic polycarboxylic acid was prepared. The acid form of Dowex ion exchange resin HCR-S-H was added with stirring to the salt solution until the pH was between 1.9 and 2.1. The resin was separated from the solution by vacuum filtration followed by a slight wash. The resulting free-acid form of the cycloaliphatic polycarboxylic acid compound was roto-evaporated twice to dryness using isopropanol as an azeotrope and further dried using toluene as an azeotrope. The free acid was esterified by placing 2.46 g (10 mmoles) of CPTA into a round bottom flask and adding 30 ml of 12% boron trifluoride-methanol complex in methanol (approximately 50 mmoles) and 20 ml methanol. The mixture was refluxed for 2 hours, the solvent evaporated and the residue cooled in an ice bath. The solution was made slightly basic with ammonium hydroxide, concentrated sodium chloride solution was added and the aqueous phase was extracted with methylene chloride. The extract was dried over calcium sulfate and evaporated. One gram of the crude reaction mixture was loaded onto a 25×300 mm liquid chromatography column prepared from 60–200 mesh silicagel. The esterified compounds were eluted with methylene chloride containing 0.5% methanol.

The resultant tetramethyl esters of CPTA were chromatographed on a 3% OV-1, 3 mm internal diameter, 2.5 meter (80–100 mesh Supelcoport) column with helium as the carrier gas at a flow rate of 40 ml/min with a flame ionization detector. A biphasic temperature program was used where the initial phase was from 140° C. to 158° C. at 3° C./min and the the final phase was from 158° C. to 225° C. at 6° C./min. The results indicated that a yield of 39 mmoles of ctct CPTA $(Li^+)_4$ (approximately 96% based on starting material) was obtained.

Halogenation of ctct CPTA to ctct CPTC

The ctct-CPTA $(Li^+)_4$ was halogenated by mixing 5.9 g (21.9 mmoles) with 176 mmoles phosphorous pentachloride and 100 ml n-heptane. The mixture was stirred continuously while the temperature was gradually elevated to 65° C. Stirring was continued for 4 hours at 65° C. After cooling to room temperature, the solution was suction filtered through a coarse paper and then roto-evaporated to an oil several times using additional portions of toluene. The oil was given high vacuum for an additional ½ hour and then extracted with several 200 ml portions of anhydrous heptane. The final yield of the acid chloride was 4.6 g (14.4 mmoles) which corresponds to a 73% yield of material based on ctct CPTA.

Alternatively, the tetrasodium salt of CPTA can be prepared by reacting the free acid of CPTA with an aqueous solution of sodium hydroxide. The pH is adjusted to 9 with sodium hydroxide before the reactor step.

PREPARATION EXAMPLE C 1,2,4-cyclopentane tricarboxylic acid chloride (CPTrC) was prepared by the following method.

Oxidation of 5-vinyl 2-norbornene to CPTrA Intermediate 178 g of sodium periodate and 0.86 g of ruthenium trichloride catalyst were mixed in 312 ml deionized water in a 2-liter flask fitted with mechanical stirrer, reflux condenser, thermometer and addition funnel. After partial dissolution with stirring, 280 ml acetonitrile was introduced. The flask was placed in an ice bath and a solution of 10 g of 5-vinyl 2-norbornene in 280 ml carbon tetrachloride was added dropwise with continued stirring. The temperature during the addition step did not exceed 15°–20° C. The flask was placed in a heating mantle and the reaction was heated to 60° C. gradually over a 2½-hour period and then kept at approximately 60° C. for an additional 6 hours.

A heterogeneous mixture containing yellow-green liquid and fine gray solids was roto-evaporated to near dryness under vacuum at room temperature. The mixture was roto-evaporated two more times to dryness using 250 ml portions of acetonitrile with a gradual increase in temperature to 55° C. under approximately 0.2 mm Hg vacuum. The dry solids were then broken up and thoroughly mixed in 250 ml of methyl ethyl ketone. The suspension was suction filtered through a 600 ml 90M fritted glass funnel. The clear amber filtrate was then roto-evaporated to a glassy residue at 55° C. under vacuum. The product was further dried overnight under vacuum at 50° C. yielding 19.18 g of crude product. The solids were broken up to fine particles in carbon tetrachloride and then filtered. This step was repeated and the solids were dried under vacuum at 50° C. to yield 15.9 g of product having a melting point of approximately 110° C.

Determination of Isomeric Forms of CPTrA Intermediate

Gas chromotography analysis performed on an esterified sample of the product (as described in Preparation Example C) revealed an approximate 75:25 mixture of all-cis and 1-cis, 2-trans, 4-cis isomers, respectively, of CPTrA.

Halogenation of CPTrA to CPTrC

The CPTrA product was halogenated in a manner similar to that described above in Preparation Example B. The phosphorous pentachloride:CPTrA stoichiometry was adjusted to account for the trifunctional carboxylic acid group and a 60° C. reaction temperature was used. The heptane-extracted 1-cis, 2-trans, 4-cis CPTrC was vacuum distilled over a range of 90°–120° C. under a 0.1 mm Hg vacuum (measured at room temperature).

PREPARATION EXAMPLE D 1-cis, 2-trans, 4-cis CPTrC was prepared by adding 8.0 g of predominantly all-cis CPTrA slowly to a chilled solution of 4.48 g of lithium hydroxide in 50 ml deionized water. The solution, having a pH of 9.0, was loaded into a stainless steel Parr reactor as described above in Preparation Example B. The solution was heated at 250° C. for 4½ hours during which a pressure of approximately 525 psi was maintained. The workup and drying of this product was identical to that described previously for ctct CPTA($Li^+$)$_4$. The amount of dry 1-cis, 2-trans, 4-cis CPTrA($Li^+$)$_3$ salt recovered was 8.6 g.

Halogenation of the product to 1-cis, 2-trans, 4-cis CPTrC was performed in a manner similar to that described in Preparation Example C.

EXAMPLES 1-5

Five different membranes were prepared according to the present invention using the so-called "control frame" method using 1,2,3,4-cyclobutane tetracarboxylic acid chloride (CBTC) as the sole amine-reactive reactant or as one component of a mixture of amine-reactive reactants. A polysulfone ultra filter microporous support was mounted in a 6"×6" TEFLON ® (duPont) frame, soaked with deionized water, and the excess surface water was blown off with air. Approximately 50 ml of an aqueous amine solution was then poured on the polysulfone support for a contact time of one minute. In each of the five examples, the amine solution contained 2 wt. % metaphenylenediamine (MPD), 6.6 wt. % triethylamine camphorsulfonic acid salt (TEACSA) and 0.1 wt. % sodium dodecylbenzyl sulfonate (SDBS) surfactant which was adjusted to a pH of 7.0 with HCl. After the one minute contact time, the amine solution was drained off vertically for 30 seconds. Approximately 50ml of an acyl halide (—COCl) solution in ISOPAR ® (an isoparaffin mixture from Exxon Corp.) solvent containing the respective acyl halides set forth in Table I was then poured onto the liquid layer of polyamine solution and allowed to remain for 30 seconds. The acyl halide solution was then drained off vertically for 30 seconds, and the support was finally dried in an air oven for six minutes at 100° C.

The performance of the resulting water permeable membranes was measured by passing an aqueous solution containing about 2,000 ppm of NaCl (pH 7.0) through each membrane at 225 psig. The salt rejection and flux rate for each of the membranes are also set forth in Table I.

TABLE I

| AMINE-REACTIVE REACTANT CONTAINING CBTC | | | | | |
|---|---|---|---|---|---|
| Ex. No. | 1 | 2 | 3 | 4 | 5 |
| Total —COCl (wt/vol %) | 0.085 | 0.085 | 0.1075 | 0.15 | 0.15 |
| CBTC   relative | 100 | 60 | 79.1 | 28.4 | 25.7 |
| IPC    } % of | 0 | 0 | 20.9 | 62.8 | 56.7 |
| TMC    —COCl | 0 | 40 | 0 | 8.8 | 17.6 |
| Rejection (%) | 99.29 | 99.47 | 99.40 | 99.70 | 99.79 |
| Flux (gfd) | 30.3 | 30.1 | 19.7 | 23.2 | 23.8 |

EXAMPLES 6-14

Nine membranes containing CPTC as at least one of the acyl halides for the amine-reactive reactant were prepared by a method similar to that used for Examples 1-5, except that a soft cloth sheet was dipped into the polyamine solution and applied to the polysulfone support. The support surface was drained for a total of 46 seconds. The excess amine solution was wiped off with a rubber wiper blade and drained diagonally for an additional 21 seconds. The contact time for the acyl halide solution was 6 seconds, after which the surface was drained vertically for 2 minutes. The identity and the amount of each of the components of the polyamine and acyl halide (—COCl) solutions are set forth in Table II. The nine membranes were tested in the same manner as in Examples 1-5, and the salt rejection and flux rates are also set forth in Table II.

TABLE II

| | AMINE-REACTIVE REACTANT CONTAINING CPTC - MACHINE METHOD | | | | | | | | |
|---|---|---|---|---|---|---|---|---|---|
| Ex. No. | 6 | 7 | 8 | 9 | 10 | 11 | 12 | 13 | 14 |
| Total —COCl (wt/vol %) | 0.07 | 0.18 | 0.113 | 0.067 | 0.08 | 0.10 | 0.123 | 0.16 | 0.19 |
| CPTC   relative | 100 | 28.4 | 80 | 100 | 100 | 100 | 81.6 | 62.5 | 52.6 |
| IPC    } % of | 0 | 62.8 | 20 | 0 | 0 | 0 | 18.4 | 37.5 | 47.4 |
| TMC    —COCl | 0 | 8.8 | 0 | 0 | 0 | 0 | 0 | 0 | 0 |
| MPD (%) | 3 | 3 | 3 | 3 | 3 | 3 | 3 | 3 | 3 |
| TEACSA (%) | 6.6 | 6.6 | 4.95 | 4.95 | 4.95 | 4.95 | 4.95 | 4.95 | 4.95 |
| Surfactant | 0.1% SDBS | 0.1% SLS | 0.15% SDBS | 0.15% SDBS | 0.15% SDBS | 0.15% SDBS | 0.15% SDBS | 0.15% SDBS | 0.15 SDBS |
| pH | 7.5 | 7.0 | 7.5 | 7.5 | 7.5 | 7.5 | 7.5 | 7.5 | 7.5 |
| Rejection (%) | 99.36 | 99.78 | 99.47 | 99.40 | 99.44 | 99.41 | 99.62 | 99.79 | 99.84 |
| Flux (gfd) | 45.0 | 27.5 | 40.1 | 47.8 | 46.7 | 31.3 | 36.3 | 26.3 | 20.9 |

EXAMPLES 15-18

Four more laboratory examples were run using CPTC as at least one of the components of the amine-reactive reactant and using essentially the same method as for Examples 6-14, except that the polyamine solution was drained 14 seconds diagonally and another 42 second diagonally after reversing direction, and there was no additional drain after wiping off the excess amine solution with the rubber wiper blade. Also, the contact time for the acyl chloride (—COCl) solution was 18 seconds and the drain time for the acyl chloride solution was 1.5 minutes. The resulting membranes were tested in the same manner as the previous Examples with approximately 2,000 ppm NaCl solution. The details of the reactants and the rejection and flux rates from the tests are set forth in Table III.

TABLE III
AMINE-REACTIVE REACTANTS CONTAINING CPTC-S METHOD

| Ex. No. | 15 | 16 | 17 | 18 |
|---|---|---|---|---|
| Total —COCl (wt/vol %) | .085 | .075 | 0.18 | 0.13 |
| CPTC  relative | 100 | 60 | 28.3 | 38.5 |
| IPC   % of | 0 | 0 | 62.8 | 36.9 |
| TMC   —COCl | 0 | 40 | 8.9 | 24.6 |
| MPD (%) | 3 | 3 | 3 | 3 |
| TEACSA (%) | 4.95 | 6.6 | 4.95 | 4.95 |
| Surfactant | 0.1% SDBS | 0.1% SDBS | 0.1% SDBS | 0.1% SLS |
| pH | 7.5 | 7.5 | 7.0 | 7.0 |
| Rejection (%) | 99.33 | 99.37 | 99.91 | 99.81 |
| Flux (gfd) | 38.0 | 40.1 | 20.0 | 25.6 |

EXAMPLES 19-21

Three pilot plant membranes were prepared using essentially the method of Examples 6-14 described above, except that the polyamine-coated substrate was passed upside down into a trough of the acyl halide (—COCl) solution and was supported on its backside by a roller. In examples 19 and 20, the aqueous polyamine solution contained 3 wt. % MPD, 4.95 wt. % TEACSA, and 0.15 wt. % SDBS adjusted to a pH of 7.5. The aqueous polyamine solution of example 21 consisted of the same formulation with the exception of 6.6 wt. % TEACSA. The resulting membranes were tested overnight in the same manner as indicated above using 0.2% NaCl solution. The details of the reactants and the test results are set forth in Table IV.

TABLE IV
AMINE-REACTIVE REACTANT CONTAINING CPTC - PILOT MACHINE METHOD

| Ex. No. | 19 | 20 | 21 |
|---|---|---|---|
| Total —COCL (wt/vol %) | 0.18 | 0.36 | 0.14 |
| CPTC  relative | 28.4 | 28.4 | 100 |
| IPC   % of | 62.8 | 62.8 | 0 |
| TMC   —COCl | 8.8 | 8.8 | 0 |
| Rejection (%) | 97.77 | 99.60 | 99.21 |
| Flux (gfd) | 20.0 | 20.3 | 43.40 |

EXAMPLES 22-25

Four more laboratory Examples were run by the same method as used for Examples 6-14 above in order to demonstrate the effect of omission of the amine salt and the addition of the aromatic polyfunctional acyl halide. In all of these Examples, the aqueous polyamine solution contained 3% MPD and 0.15% SDBS adjusted to a pH of 7.5 with HCl. The details of the reactants and the test results using approximately 2,100 ppm NaCl are given in Table V.

TABLE V
EFFECTS OF TEACSA OMISSION AND IPC ADDITION

| Ex. No. | 22 | 23 | 24 | 25 |
|---|---|---|---|---|
| Total —COCL (wt/vol %) | 0.09 | 0.09 | 0.18 | 0.18 |
| CPTC  relative | 100 | 100 | 50 | 50 |
| IPC   % of —COCL | 0 | 0 | 50 | 50 |
| TEACSA (%) | 4.95 | 0 | 4.95 | 0 |
| Rejection (%) | 99.43 | 98.78 | 99.76 | 99.03 |
| Flux (gfd) | 37.5 | 10.1 | 21.1 | 6.0 |

From Examples 22-25, the importance of the amine salt additive can be seen. In particular, the addition of the amine salt (TEACSA) in Examples 22 and 24 resulted in a more than three fold increase in the flux rate as compared to Examples 23 and 25. There was also some improvement in the salt rejection rate with the amine salt additive in Examples 22 and 24 compared to the salt rejection rates in Examples 23 and 25 without the amine salt additive.

The above Examples also show the effect of using an aromatic polyfunctional acyl halide in addition to or as replacement for part of the cycloaliphatic acyl halides. In particular, while the presence of the aromatic polyfunctional acyl halide appears to increase the rate of salt rejection somewhat, it also appears to reduce the flux rates. This result is somewhat similar to reports in the literature, such as the Arthur publication in *Journal of Membrane Science* cited above, which indicates that membranes prepared with aromatic polyfunctional acyl halides such as TMC yield higher salt rejections, but lower flux rates, than membranes prepared with aliphatic acyl halides such as cyclohexanetricarbonyl chloride.

EXAMPLES 26-34

Nine laboratory examples were run using ctct CPTC as at least one of the components of the amine-reactive reactant and using essentially the same method as for Examples 6-14. The resulting membranes were tested in the same manner as the previous examples with an approximately 2,000 ppm NaCl solution. The reactant concentrations and the test results are set forth in Table VI.

TABLE VI
AMINE-REACTIVE REACTANTS CONTAINING ctct CPTC - MACHINE METHOD

| Ex. No. | 26 | 27 | 28 | 29 | 30 | 31 | 32 | 33 | 34 |
|---|---|---|---|---|---|---|---|---|---|
| Total —COCl (wt/vol %) | .10 | .08 | .08 | .08 | .08 | .08 | .08 | .14 | .10 |
| ctct CPTC  relative | 100 | 100 | 100 | 100 | 100 | 100 | 100 | 57 | 100 |
| IPC   % of —COCl | 0 | 0 | 0 | 0 | 0 | 0 | 0 | 43 | 0 |

TABLE VI-continued

| AMINE-REACTIVE REACTANTS CONTAINING ctct CPTC - MACHINE METHOD | | | | | | | | | |
|---|---|---|---|---|---|---|---|---|---|
| Ex. No. | 26 | 27 | 28 | 29 | 30 | 31 | 32 | 33 | 34 |
| MPD (%) | 2.5 | 3 | 3 | 3 | 3 | 3 | 2.5 | 3 | 3 |
| TEACSA (%) | 5.78 | 4.95 | 4.95 | 4.95 | 4.95 | 4.95 | 4.95 | 4.95 | 4.95 |
| SDBS (%) | .125 | .15 | .15 | .15 | .15 | .15 | .15 | .15 | .15 |
| pH | 7.5 | 10.0 | 7.5 | 7.5 | 7.5 | 7.5 | 7.5 | 7.5 | 7.5 |
| Rejection (%) | 99.83 | 99.60 | 99.72 | 99.84 | 99.81 | 99.84 | 99.86 | 99.84 | 99.72 |
| Flux (gfd) | 17.0 | 25.6 | 22.2 | 17.7 | 20.7 | 23.7 | 21.1 | 18.7 | 25.1 |

EXAMPLES 35-41

Seven pilot plant membranes were prepared using the method of Examples 19-21 described above. The aqueous polyamine solution contained 3 wt. % MPD, 4.9 wt. % TEACSA and 0.15 wt. % SDBS adjusted to a pH of 7.5. The resulting membranes were tested overnight in the same manner as indicated above using 0.2% NaCl solution. The details of the reactant concentration and the test results are set forth in Table VII.

TABLE VII

| AMINE-REACTIVE REACTANT CONTAINING ctct CPTC - PILOT MACHINE METHOD | | | | | | | |
|---|---|---|---|---|---|---|---|
| Ex. No. | 35 | 36 | 37 | 38 | 39 | 40 | 41 |
| Ctct CPTC (wt/vol %) | .18 | .18 | .18 | .18 | .12 | .14 | .16 |
| Rejection (%) | 99.48 | 99.54 | 99.52 | 99.42 | 99.37 | 99.51 | 99.65 |
| Flux (gfd) | 24.6 | 26.0 | 28.8 | 31.4 | 28.6 | 24.1 | 21.2 |

EXAMPLES 42-47

Four laboratory examples were run using ctc CPTrC as the sole amine-reactive reactant and using essentially the same method as for Examples 6-14. In all of these examples, the aqueous polyamine solution contained 3 wt. % MPD, 4.95 wt. % TEACSA and 0.15 wt. % SDBS adjusted to a pH of 7.5. The resulting membranes were tested in the same manner as the previous examples with an approximately 2,000 ppm NaCl solution. The reactant concentrations and the test results are set forth in Table VIII.

TABLE VIII

| AMINE-REACTIVE REACTANT CONTAINING ctc CPTrC - MACHINE METHOD | | | | | | |
|---|---|---|---|---|---|---|
| Ex. No. | 42 | 43 | 44 | 45 | 46 | 47 |
| ctc CPTrC (wt/vol %) | .08 | .08 | .08 | .12 | .12 | .12 |
| Rejection (%) | 99.75 | 99.74 | 99.69 | 99.75 | 99.81 | 99.7 |
| Flux (gfd) | 15.1 | 14.4 | 19.4 | 11.3 | 11.2 | 15.5 |

EXAMPLES 48-54

Seven production machine-run membranes were prepared using ctct CPTC as at least one of the components of the amine-reactive reactant and using essentially the same method as for Examples 6-14. In all of these examples, the aqueous polyamine solution contained 2 wt. % MPD, 6.6 wt. % TEACSA and 0.15 wt. % SLS adjusted to a pH of 8.5. The drying step was at 140° C.

The performance of the resulting membranes was measured by passing an aqueous solution containing 1,500 ppm of NaCl (pH 6.5) through each membrane at 215 psig. The reactant concentrations and the test results are set forth in Table IX.

TABLE IX

| AMINE-REACTIVE REACTANTS CONTAINING ctct CPTC - MACHINE METHOD | | | | | | | |
|---|---|---|---|---|---|---|---|
| Ex. No. | 48 | 49 | 50 | 51 | 52 | 53 | 54 |
| Total —COCl (wt/wt %) | .16 | .16 | .16 | .16 | .16 | .16 | .16 |
| ctct CPTC relative % of —COCl | 37.5 | 37.5 | 37.5 | 37.5 | 37.5 | 37.5 | 37.5 |
| IPC relative % of —COCl | 62.5 | 62.5 | 62.5 | 62.5 | 62.5 | 62.5 | 62.5 |
| Rejection (%) | 99.75 | 99.74 | 99.67 | 99.63 | 99.76 | 99.73 | 99.72 |
| Flux (gfd) | 16.7 | 16.0 | 17.2 | 18.5 | 19.2 | 17.7 | 17.5 |

The present invention may be embodied in other specific forms without departing from the spirit or essential attributes thereof and, accordingly, reference should be made to the appended claims, rather than to the foregoing specification, as indicating the scope of the invention.

We claim:

1. A water permeable membrane prepared by interfacially polymerizing, on a microporous support, (1) an essentially monomeric polyamine reactant having at least two amine functional groups per reactant molecule, and (2) an essentially monomeric amine-reactive reactant comprising a polyfunctional single ring cycloaliphatic acyl halide having fewer than 6 carbon atoms per ring, or mixture thereof, wherein the amine-reactive reactant has, on the average, at least about 2.2 acyl halide groups per reactant molecule.

2. The water permeable membrane as claimed in claim 1, wherein polymerization occurs in the presence of a monomeric amine salt.

3. The water permeable membrane as claimed in 1, wherein said water permeable membrane is produced by the process comprising the steps of:
   (a) coating a microporous support with an aqueous solution comprising an essentially monomeric polyamine reactant having at least two amine functional groups to form a liquid layer on said microporous support;
   (b) contacting said liquid layer with an organic solvent solution of an essentially monomeric amine-reactive reactant comprising said polyfunctional cycloaliphatic acyl halide or mixture thereof; and
   (c) drying the product of step (b) so as to form said water permeable membrane.

4. The water permeable membrane as claimed in claim 3, wherein said aqueous polyamine solution also contains a monomeric amine salt.

5. The water permeable membrane as claimed in claim 1, wherein said water permeable membrane is produced by the process comprising the steps of:
  (a) coating a microporous support with a first aqueous solution comprising a monomeric amine salt to form a monomeric amine salt layer on said microporous support;
  (b) coating said monomeric amine salt layer with a second aqueous solution comprising an essentially monomeric polyamine reactant having at least two amine functional groups to form a liquid layer on said monomeric amine salt layer;
  (c) coating said liquid layer with an organic solvent solution of an essentially monomeric amine-reactive reactant comprising said polyfunctional cycloaliphatic acyl halide or mixture thereof; and
  (d) drying the product of step (c) so as to form said water permeable membrane.

6. The water permeable membrane as claimed in claim 1, wherein said monomeric amine salt is represented by formula (I) or (II):

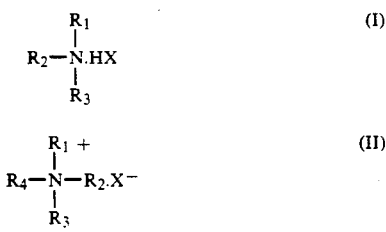

wherein $R_1$, $R_2$, $R_3$ and $R_4$, which may be the same or different, each represents a hydrocarbon; X represents a member selected from the group consisting of a halide, a nitrate, a sulfate, a phosphate, a sulfonate, a carboxylate, a halogenated carboxylate and an oxygenated haloacid derivative; and HX represents a strong acid which forms a water soluble salt with

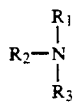

7. The water permeable membrane as claimed in claim 1, wherein said amine functional groups are primary amine functional groups.

8. The water permeable membrane as claimed in claim 1, wherein said polyamine reactant is at least one member selected from the group consisting of an aromatic primary diamine and substituted derivatives thereof; an aromatic primary triamine; an aromatic secondary diamine; a cycloaliphatic primary diamine; a cycloaliphatic secondary diamine; and a xylylene primary diamine.

9. The water permeable membrane as claimed in claim 1, wherein said cycloaliphatic acyl halide is selected from cyclobutane and cyclopentane acyl halides.

10. The water permeable membrane as claimed in claim 9 wherein said acyl halide has a functionality on the average of from about 3 to about 4 acyl halide groups per reactant molecule.

11. The water permeable membrane as claimed in claim 10, wherein said acyl halide is 1,2,3,4-cyclopentane tetracarboxylic acid chloride.

12. The water permeable membrane as claimed in claim 11, wherein said acyl halide is 1-cis, 2-trans, 3-cis, 4-trans-cyclopentane tetracarboxylic acid chloride.

13. The water permeable membrane as claimed in claim 10, wherein said acyl halide is 1,2,3,4-cyclobutane tetracarboxylic acid chloride.

14. The water permeable membrane as claimed in claim 13, wherein said acyl halide is 1-cis, 2-trans, 3-cis, 4-trans-cyclobutane tetracarboxylic acid chloride.

15. The water permeable membrane as claimed in claim 10, wherein said acyl halide is 1,2,4-cyclopentane tricarboxylic acid chloride.

16. The water permeable membrane as claimed in claim 15, wherein said acyl halide is 1-cis, 2-trans, 4-cis-cyclopentane tricarboxylic acid chloride.

17. The water permeable membrane as claimed in claim 10, wherein said acyl halide is 1,2,3-cyclobutane tricarboxylic acid chloride.

18. The water permeable membrane as claimed in claim 17, wherein said acyl halide is 1-cis, 2-trans, 3-cis-cyclobutane tricarboxylic acid chloride.

19. The water permeable membrane as claimed in claim 1 wherein up to about 90 weight percent of said polyfunctional cycloaliphatic acyl halide is replaced by an essentially monomeric, aromatic polyfunctional acyl halide having at least 2 acyl halide groups per reactant molecule.

20. The water permeable membrane as claimed in claim 19, wherein said aromatic acyl halide is selected from the group consisting of isophthaloyl chloride, trimesoyl chloride, terephthaloyl chloride, and mixtures thereof.

21. A water permeable membrane prepared by interfacially polymerizing on a microporous support (1) metaphenylenediamine and (2) 1-cis, 2-trans, 3-cis, 4-trans-cyclopentane tetracarboxylic acid halide in the presence of (3) the amine salt of triethylamine and camphorsulfonic acid.

22. A water permeable membrane as claimed in claim 21, wherein up to about 90 weight percent of said acid halide reactant is replaced with isophthaloyl chloride, trimesoyl chloride, and/or terephthaloyl chloride.

23. A process for producing a water permeable membrane comprising interfacially polymerizing, on a microporous support, (1) an essentially monomeric polyamine reactant having at least two amine functional groups per reactant molecule, and (2) an essentially monomeric amine-reactive reactant comprising a polyfunctional single ring cycloaliphatic acyl halide having fewer than 6 carbon atoms in the ring, or mixture thereof, wherein the amine-reactive reactant has, on the average, at least about 2.2 acyl halide groups per reactant molecule.

24. The process as claimed in claim 23, wherein polymerization occurs in the presence of a monomeric amine salt.

25. The process as claimed in claim 24, wherein said water permeable membrane is produced by the process comprising the steps of:
  (a) coating a microporous support with an aqueous solution comprising an essentially monomeric polyamine reactant having at least two amine functional groups to form a liquid layer on said microporous support;
  (b) contacting said liquid layer with an organic solvent solution of an essentially monomeric amine-reactive reactant comprising said polyfunctional acyl halide or mixture thereof, and (c) drying the product of step (b) so as to form said water permeable membrane.

26. The process as claimed in claim 25, wherein said aqueous polyamine solution also contains a monomeric amine salt.

27. The process as claimed in claim 23, wherein said water permeable membrane is produced by the process comprising the steps of:
   (a) coating a microporous support with a first aqueous solution comprising a monomeric amine salt to form a monomeric amine salt layer on said microporous support;
   (b) coating said monomeric amine salt layer with a second aqueous solution comprising an essentially monomeric polyamine reactant having at least two amine functional groups to form a liquid layer on said monomeric amine salt layer;
   (c) coating said liquid layer with an organic solvent solution of an essentially monomeric amine-reactive reactant comprising said polyfunctional acyl halide or mixture thereof; and
   (d) drying the product of step (c) so as to form said water permeable membrane.

28. The process as claimed in claim 23, wherein said monomeric amine salt is represented by formula (I) or (II):

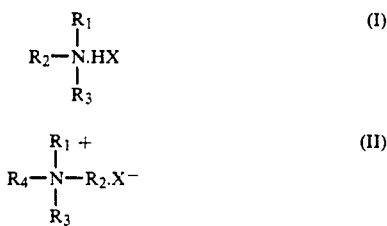

wherein $R_1$, $R_2$, $R_3$ and $R_4$, which may be the same or different, each represents a hydrocarbon; X represents a member selected from the group consisting of a halide, a nitrate, a sulfate, a phosphate, a sulfonate, a carboxylate, a halogenated carboxylate and an oxygenated haloacid derivative; and HX represents a strong acid which forms a water soluble salt with

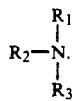

29. The process as claimed in claim 23, wherein said amine functional groups are primary amine functional groups.

30. The process as claimed in claim 23, wherein said polyamine reactant is at least one member selected from the group consisting of an aromatic primary diamine and substituted derivatives thereof; an aromatic primary triamine; an aromatic secondary diamine; a cycloaliphatic primary diamine; a cycloaliphatic secondary diamine; and a xylylene primary diamine.

31. The process as claimed in claim 23, wherein said cycloaliphatic acyl halide is selected from cyclobutane and cyclopentane acyl halides.

32. The process as claimed in claim 31 wherein said acyl halide has a functionality on the average of from about 3 to about 4 acyl halide groups per reactant molecule.

33. The process as claimed in claim 23, wherein said acyl halide is 1,2,3,4-cyclopentane tetracarboxylic acid chloride.

34. The process as claimed in claim 33, wherein said acyl halide is 1-cis, 2-trans, 3-cis, 4-trans-cyclopentane tetracarboxylic acid chloride.

35. The process as claimed in claim 23, wherein said acyl halide is 1,2,3,4-cyclobutane tetracarboxylic acid chloride.

36. The process as claimed in claim 35, wherein said acyl halide is the 1-cis, 2-trans, 3-cis, 4-trans-cyclobutane tetracarboxylic acid chloride.

37. The process as claimed in claim 23, wherein said acyl halide is 1,2,4-cyclopentane tricarboxylic acid chloride.

38. The process as claimed in claim 37, wherein said acyl halide is a 1-cis, 2-trans, 4-cis-cyclopentane tricarboxylic acid chloride.

39. The process as claimed in claim 23, wherein said acyl halide is 1,2,3-cyclobutane tricarboxylic acid chloride.

40. The process as claimed in claim 39, wherein said acyl halide is a 1-cis, 2-trans, 3-cis-cyclobutane tricarboxylic acid chloride.

41. The process as claimed in claim 23 wherein up to about 90 weight percent of said polyfunctional cycloaliphatic acyl halide is replaced by an essentially monomeric, aromatic polyfunctional acyl halide having at least 2 acyl halide groups per reactant molecule.

42. The process as claimed in claim 23, wherein said aromatic acyl halide is selected from the group consisting of isophthaloyl chloride, trimesoyl chloride, terephthaloyl chloride, and mixtures thereof.

43. A process for preparing a water permeable membrane, comprising interfacially polymerizing on a microporous support (1) metaphenylene diamine and (2) 1-cis, 2-trans, 3-cis, 4-trans-cyclopentane tetracarboxylic acid halide in the presence of (3) triethylamine camphorsulfonic acid salt.

44. The process as claimed in claim 43, wherein up to about 90 weight percent of said acid halide is replaced with isophthaloyl chloride, trimesoyl chloride, and/or terephthaloyl chloride.

45. A process for desalination of brackish water or sea water comprising passing the water under pressure through a membrane according to claim 1.

46. A process for desalination of brackish, water or sea water comprising passing the water under pressure through a membrane according to claim 21.

47. The 1-cis, 2-trans, 3-cis, 4-trans isomer of cyclopentane tetracarboxylic acid chloride.

48. The 1-cis, 2-trans, 4-cis isomer of cyclopentane tricarboxylic acid chloride.

49. The 1-cis, 2-trans, 3-cis, 4-trans isomer of cyclobutane tetracarboxylic acid chloride.

50. The 1-cis, 2-trans, 3-cis isomer of cyclobutane tetracarboxylic acid chloride.

51. A process for preparing an alternating cis/trans isomer of a cycloaliphatic polycarboxylic acid halide comprising the steps of:
   a) converting an all-cis isomer of a cycloaliphatic polycarboxylic acid to a metal salt thereof by reacting the all-cis isomer with a metal hydroxide;
   b) heating the metal salt under pressure to convert the all-cis isomer of the polycarboxylic acid metal salt to the alternating cis/trans isomer thereof;

c) halogenating the carboxylic acid metal salt groups of the alternating cis/trans isomer to the acid halide form thereof; and d) recovering the alternating cis/trans isomer of the cycloaliphatic polycarboxylic acid halide.

52. The process as claimed in claim 51 wherein the halide is chloride.

53. The process as claimed in claim 51 wherein the metal hydroxide is selected from the group consisting of sodium, potassium, lithium, calcium and iron hydroxides.

54. The process as claimed in claim 51 wherein the heating step is carried out at a temperature of at least about 150° C.

55. The process as claimed in claim 51 wherein the pressure is generated autogenously by heating in a closed vessel.

* * * * *